US00PP27055P2

(12) United States Plant Patent
Hofmann et al.

(10) Patent No.: US PP27,055 P2
(45) Date of Patent: Aug. 9, 2016

(54) ***CLEOME* PLANT NAMED 'INCLESRCAR'**

(50) Latin Name: *Cleome hybrida*
Varietal Denomination: Inclesrcar

(71) Applicants: Silvia Hofmann, Mainz (DE); Friedhelm Leuchtenberger, Lingen (DE)

(72) Inventors: Silvia Hofmann, Mainz (DE); Friedhelm Leuchtenberger, Lingen (DE)

(73) Assignee: Innovaplant Zierpflanzen GmbH & Co KG, Gensingen (DE)

( * ) Notice: Subject to any disclaimer, the term of this patent is extended or adjusted under 35 U.S.C. 154(b) by 1 day.

(21) Appl. No.: 14/544,632

(22) Filed: Jan. 23, 2015

(51) Int. Cl.
*A01H 5/02* (2006.01)

(52) U.S. Cl.
USPC ..... Plt./416

(58) Field of Classification Search
USPC ..... Plt./416
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Cleome* plant named 'Inclesrcar', characterized by its upright plant habit; freely branching habit; dense and bushy plant form; freely flowering habit; pink-colored flowers; and good garden performance.

1 Drawing Sheet

Botanical designation: *Cleome hybrida.*
Cultivar denomination: 'INCLESRCAR'.

BACKGROUND OF THE INVENTION

The present invention relates to a new and distinct cultivar of *Cleome* plant, botanically known as *Cleome hybrida* and hereinafter referred to by the name 'Inclesrcar'.

The new *Cleome* plant is a naturally-occurring whole plant mutation of *Cleome hybrida* 'Inncleosr', disclosed in U.S. Plant Pat. No. 19,733. The new *Cleome* plant was discovered and selected by the Inventors as a flowering plant from within a population of plants of 'Inncleosr' in a controlled greenhouse environment in Lingen, Germany in May, 2013.

Asexual reproduction of the new *Cleome* plant by cuttings in a controlled greenhouse environment in Heidesheim, Germany since July, 2013 has shown that the unique features of this new *Cleome* plant are stable and reproduced true to type in successive generations.

SUMMARY OF THE INVENTION

Plants of the new *Cleome* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inclesrcar'. These characteristics in combination distinguish 'Inclesrcar' as a new and distinct *Cleome* plant:

1. Upright plant habit.
2. Freely branching habit; dense and bushy plant form.
3. Freely flowering habit.
4. Pink-colored flowers.
5. Good garden performance.

Plants of the new *Cleome* differ primarily from plants of the mutation parent, 'Inncleosr', in flower bud and flower color as plants of 'Inncleosr' have pinkish purple-colored flower buds and more intense pink-colored flowers than plants of the new *Cleome.*

Plants of the new *Cleome* can be compared to plants of *Cleome hybrida* 'Inclesnabl', disclosed in U.S. Plant patent application Ser. No. 13/573,174 (Abandoned). In side-by-side comparisons conducted in Heidesheim, Germany, plants of the new *Cleome* and 'Inclesnabl' differed in the following characteristics:

1. Plants of the new *Cleome* and 'Inclesnabl' differed in flower bud color as plants of 'Inclesnabl' had blush pink-colored flower buds.
2. Plants of the new *Cleome* and 'Inclesnabl' differed in flower color as plants of 'Inclesnabl' had white-colored flowers blushed with light pink towards the apex.

Plants of the new *Cleome* can also be compared to plants of *Cleome hybrida* 'Linde Armstrong', not patented. In side-by-side comparisons conducted in Heidesheim, Germany, plants of the new *Cleome* and 'Linde Armstrong' differed in the following characteristics:

1. Plants of the new *Cleome* were larger and more vigorous than plants of 'Linde Armstrong'.
2. Plants of the new *Cleome* were more freely branching than plants of 'Linde Armstrong'.
3. Plants of the new *Cleome* and 'Linde Armstrong' differed in leaf color as plants of 'Linde Armstrong' had reddish green-colored leaves.
4. Plants of the new *Cleome* and 'Inclesnabl' differed in flower bud color as plants of 'Linde Armstrong' had rose pink-colored flower buds.

BRIEF DESCRIPTION OF THE PHOTOGRAPHS

The accompanying colored photographs illustrate the overall appearance of the new *Cleome* plant showing the colors as true as it is reasonably possible to obtain in colored reproductions of this type. Colors in the photographs may differ slightly from the color values cited in the detailed botanical description which accurately describe the colors of the new *Cleome* plant.

The photograph at the bottom of the sheet comprises a side perspective view of a typical flowering plant of 'Inclesrcar' grown in a container.

The photograph at the top of the sheet is a close-up view of a typical flowering plant of 'Inclesrcar'.

DETAILED BOTANICAL DESCRIPTION

The aforementioned photographs and following observations, measurements and values describe plants grown during the autumn in 10-cm containers in an outdoor nursery in Bonsall, Calif. and under commercial practices typical of commercial *Cleome* production. During the production of the plants, day temperatures ranged from 16.6° C. to 29.4° C., night temperatures ranged from 12.8° C. to 18.3° C. and light levels ranged from 3,500 to 4,500 foot-candles. Plants were pinched two times and were eight weeks old when the photographs and description were taken. Plants were grown under long day/short night conditions to induce flower initiation and development. In the following description, color references are made to The Royal Horticultural Society Colour Chart, 2007 Edition, except where general terms of ordinary dictionary significance are used.

Botanical classification: *Cleome hybrida* 'Inclesrcar'.

Parentage: Naturally-occurring whole plant mutation of *Cleome hybrida* 'Inncleosr', disclosed in U.S. Plant Pat. No. 19,733.

Propagation:

- *Type*.—By vegetative cuttings.
- *Time to initiate roots, summer*.—About five to seven days at soil temperatures about 21° C.
- *Time to initiate roots, winter*.—About seven to nine days at soil temperatures about 21° C.
- *Time to produce a rooted young plant, summer*.—About twelve days at soil temperatures about 21° C.
- *Time to produce a rooted young plant, winter*.—About 15 days at soil temperatures about 21° C.
- *Root description*.—Medium in thickness, fibrous; white in color.
- *Rooting habit*.—Moderately freely branching; medium density.

Plant description:

- *Plant and growth habit*.—Herbaceous perennial; upright plant habit; vigorous growth habit.
- *Branching habit*.—Freely branching habit, when pinched, about eight primary lateral branches each with secondary lateral branches developing.
- *Plant height*.—About 27 cm.
- *Plant width (spread)*.—About 23.5 cm.
- *Lateral branches*.—Length: About 24 cm. Diameter: About 4 mm. Internode length: About 2.6 cm. Strength: Strong. Texture: Pubescent, minute; longitudinally ridged; occasional tiny spines, close to 1 mm in length, randomly scattered on developed stems. Color: Close to 144A.

Leaf description:

- *Arrangement*.—Alternate; palmately compound with three to five leaflets per leaf.
- *Fragrance*.—None detected.
- *Leaf length*.—About 7.8 cm.
- *Leaf width*.—About 10 cm.
- *Center leaflet length*.—About 6.2 cm.
- *Center leaflet width*.—About 2.2 cm.
- *Lateral leaflets length*.—About 5.4 cm.
- *Lateral leaflets width*.—About 2 cm.
- *Lower leaflets length*.—About 3.4 cm.
- *Lower leaflets width*.—About 1.3 cm.
- *Leaflet shape*.—Elliptical.
- *Leaflet apex*.—Acute.
- *Leaflet base*.—Attenuate.
- *Leaflet margin*.—Entire.
- *Leaflet texture, upper and lower surfaces*.—Scattered pubescence; minute.
- *Venation pattern*.—Pinnate, arcuate.
- *Color*.—Developing leaflets, upper surface: Close to 146A. Developing leaflets, lower surface: Close to 146B. Fully expanded leaflets, upper surface: Close to N137C; venation, close to 147B. Fully expanded leaflets, lower surface: Close to 147B; venation, close to 147C.
- *Leaf petioles*.—Length: About 7.8 cm. Diameter: About 2.5 mm. Texture, upper and lower surfaces: Pubescent, minute. Color, upper and lower surfaces: Close to 146B.

Flower description:

- *Flower type and flowering habit*.—Single zygomorphic flowers arranged in short terminal racemes; flowers face upright to outwardly; freely flowering habit with typically about 42 flowers developing per raceme.
- *Fragrance*.—None detected.
- *Natural flowering season*.—Long flowering period; plants flower continuously from spring until frost in southern California.
- *Postproduction longevity*.—Individual flowers last about three days on the plant; flowers not persistent.
- *Flower buds*.—Height: About 1.6 cm. Diameter: About 4 mm. Shape: Narrowly elongate. Color: Close to 73D.
- *Inflorescence height*.—About 6.5 cm to 7 cm.
- *Inflorescence diameter*.—About 6.8 cm.
- *Flower diameter*.—About 2.3 cm.
- *Flower depth*.—About 2.5 cm.
- *Petals*.—Quantity per flower: Typically four in a single whorl. Length: About 1.9 cm. Width: About 7 mm. Shape: Elliptical. Apex: Broadly acute. Base: Attenuate. Margin: Entire. Texture, upper and lower surfaces: Smooth, glabrous; velvety. Color: When opening, upper surface: Close to 75B to 75D; towards the base, lighter than 75D. When opening, lower surface: Close to 75D; towards the base, close to NN155B. Fully opened, upper surface: Close to 73B to 73D; towards the base, close to NN155C; color becoming closer to 75D with development. Fully opened, lower surface: Close to 75C to 75D.
- *Sepals*.—Quantity per flower: Typically four in a single whorl. Length: About 5 mm. Width: About 1 mm. Shape: Lanceolate. Apex: Acute. Base: Truncate. Margin: Entire. Texture, upper and lower surfaces: Pubescent, minute; denser along the margins. Color, upper and lower surfaces: Close to 144A.
- *Peduncles*.—Length: About 2.6 cm. Diameter: About 2 mm. Angle: Mostly upright. Strength: Strong; flexible. Texture: Pubescent, minute. Color: Close to 146C.
- *Pedicels*.—Length: About 1.8 cm. Diameter: About 1 mm. Angle: Distal flowers, about 10° to 15° from peduncle axis; proximal flowers, about 80° from peduncle axis. Strength: Strong; flexible. Texture: Pubescent, minute. Color: Close to 152A to 152B.

*Flower bracts*.—Quantity and arrangement: One subtending each flower; sessile. Length: About 2 cm. Width: About 1 cm. Shape: Cordate. Texture, upper and lower surfaces: Smooth, glabrous. Color, upper and lower surfaces: Close to 146A.

*Reproductive organs*.—Stamens: Quantity per flower: Typically six. Filament length: About 2 mm. Filament color: Close to 146B. Anther shape: Lanceolate. Anther length: About 5 mm. Anther color: Close to 152C. Pollen amount: Scarce. Pollen color: Close to 152D. Pistils: Quantity per flower: One. Pistil length: About 2.2 cm; long and extended beyond petals, curving upwardly. Stigma shape: Rounded. Stigma color: Close to N77B. Style length: About 1.8 cm. Style color: Close to 152B. Ovary color: Close to 146C.

*Fruits and seeds*.—Fruit and seed development have not been observed on plants of the new *Cleome*.

Disease & pest resistance: Plants of the new *Cleome* have not been noted to be resistant to pathogens and pests common to *Cleome* plants.

Garden performance: Plants of the new *Cleome* have been observed to have good garden performance and tolerate rain, wind and temperatures ranging from about 1° C. to 35° C.

It is claimed:

1. A new and distinct *Cleome* plant named 'Inclesrcar' as illustrated and described.

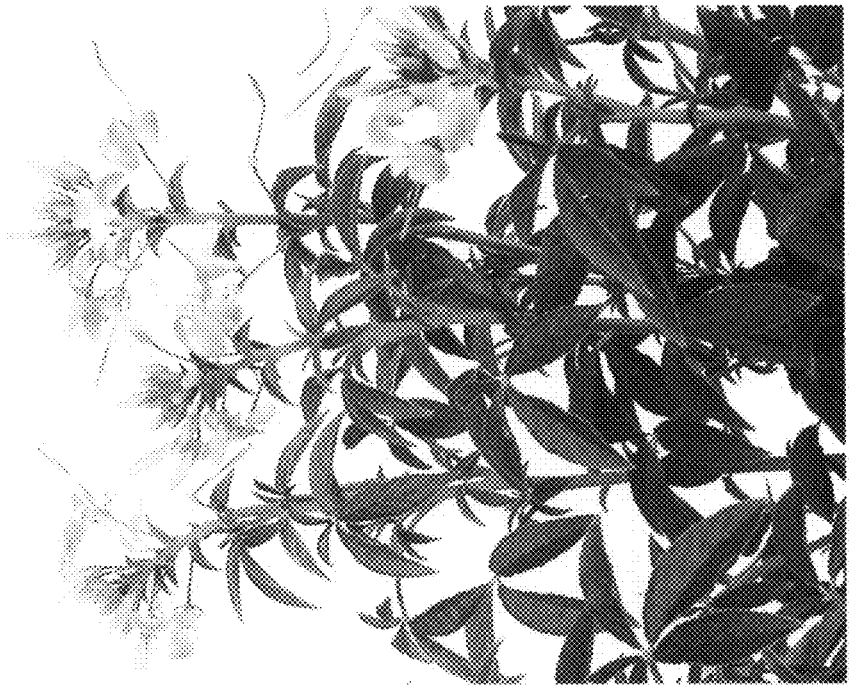
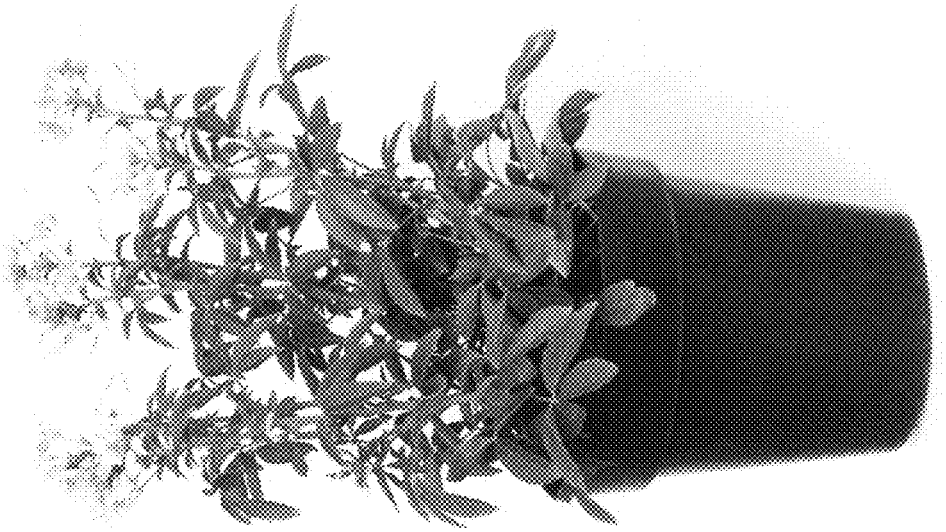

* * * * *